(12) United States Patent
Su

(10) Patent No.: US 10,264,357 B1
(45) Date of Patent: Apr. 16, 2019

(54) AUDIO FREQUENCY GENERATING DEVICE AND AUDIO FREQUENCY GENERATING METHOD

(71) Applicant: QISDA CORPORATION, Taoyuan (TW)

(72) Inventor: Chia-Hung Su, Taipei (TW)

(73) Assignee: Qisda Corporation, Taoyuan (TW)

( * ) Notice: Subject to any disclaimer, the term of this patent is extended or adjusted under 35 U.S.C. 154(b) by 0 days.

(21) Appl. No.: 16/102,757

(22) Filed: Aug. 14, 2018

(30) Foreign Application Priority Data

Jul. 24, 2018 (CN) .......................... 2018 1 0821308

(51) Int. Cl.
*H04R 3/04* (2006.01)
*H04S 1/00* (2006.01)
*H04R 5/04* (2006.01)

(52) U.S. Cl.
CPC ................ *H04R 3/04* (2013.01); *H04R 5/04* (2013.01); *H04S 1/002* (2013.01); *H04R 2430/03* (2013.01)

(58) Field of Classification Search
None
See application file for complete search history.

(56) References Cited

U.S. PATENT DOCUMENTS

| | | | | |
|---|---|---|---|---|
| 4,409,877 A | * | 10/1983 | Budelman | G10H 1/24 84/345 |
| 2008/0226093 A1 | * | 9/2008 | Kushida | H04R 3/12 381/77 |
| 2013/0016856 A1 | * | 1/2013 | Koike | G10L 21/038 381/98 |

* cited by examiner

*Primary Examiner* — Paul W Huber

(57) ABSTRACT

An audio frequency generating device includes a storage unit, a selecting unit, a processing unit, a first speaker and a second speaker. The storage unit stores at least one chord and each chord includes N fundamental frequencies. The selecting unit is electrically connected to the storage unit. The selecting unit selects M fundamental frequencies from the N fundamental frequencies of at least one of the at least one chord. The processing unit is electrically connected to the selecting unit. The processing unit uses the M fundamental frequencies to generate a first audio frequency. The processing unit uses a frequency difference to adjust each of the M fundamental frequencies to generate a second audio frequency. The first speaker is electrically connected to the processing unit and outputs the first audio frequency. The second speaker is electrically connected to the processing unit and outputs the second audio frequency.

12 Claims, 2 Drawing Sheets

AUDIO FREQUENCY GENERATING DEVICE AND AUDIO FREQUENCY GENERATING METHOD

BACKGROUND OF THE INVENTION

1. Field of the Invention

The invention relates to an audio frequency generating device and an audio frequency generating method and, more particularly, to an audio frequency generating device and an audio frequency generating method using chord to generate binaural beats.

2. Description of the Prior Art

Binaural beats are a type of audio frequency for inducing frequency-following response (FFR). When both ears of a human listen to different audio frequencies, the brainstem may be stimulated to generate specific physiological response in accordance with the frequency difference. In general, the brainwave frequency may be subdivided into several frequency bands including delta brainwave frequency band (0.5-3.5 Hz), theta brainwave frequency band (4-7 Hz), alpha brainwave frequency band (8-12 Hz), beta brainwave frequency band (13-28 Hz), and gamma brainwave frequency band (28+ Hz). Each of these frequency bands has been correlated with specific behavioral states. Delta brainwave frequency band is associated with deep sleep; theta brainwave frequency band is associated with light sleep or dreaming; alpha brainwave frequency band is associated with relaxed consciousness; and beta and gamma brainwave frequency bands are associated with active consciousness. At present, the prior art uses a single frequency to produce binaural beats. However, the single frequency is too dissonant for hearing. After listening to the single frequency for a span of time, a user may feel uncomfortable easily.

SUMMARY OF THE INVENTION

An objective of the invention is to provide an audio frequency generating device and an audio frequency generating method using chord to generate binaural beats, so as to solve the aforesaid problems.

According to an embodiment of the invention, an audio frequency generating device comprises a storage unit, a selecting unit, a processing unit, a first speaker and a second speaker. The storage unit stores at least one chord and each of the at least one chord comprises N fundamental frequencies, wherein N is a positive integer larger than one. The selecting unit is electrically connected to the storage unit. The selecting unit selects M fundamental frequencies from the N fundamental frequencies of at least one of the at least one chord, wherein M is a positive integer larger than one and smaller than or equal to N. The processing unit is electrically connected to the selecting unit. The processing unit uses the M fundamental frequencies to generate a first audio frequency. The processing unit uses a frequency difference to adjust each of the M fundamental frequencies to generate a second audio frequency. The first speaker is electrically connected to the processing unit. The first speaker outputs the first audio frequency. The second speaker is electrically connected to the processing unit. The second speaker outputs the second audio frequency.

According to another embodiment of the invention, an audio frequency generating method comprises steps of selecting M fundamental frequencies from N fundamental frequencies of at least one of at least one chord, wherein N is a positive integer larger than one and M is a positive integer larger than one and smaller than or equal to N; using the M fundamental frequencies to generate a first audio frequency; using a frequency difference to adjust each of the M fundamental frequencies to generate a second audio frequency; and outputting the first audio frequency and the second audio frequency.

As mentioned in the above, the invention uses at least two fundamental frequencies of at least one chord to generate binaural beats including the first audio frequency and the second audio frequency. Since the chord is more consonant for hearing, a user will not feel uncomfortable after listening to the binaural beats generated using the chord by the invention for a span of time.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
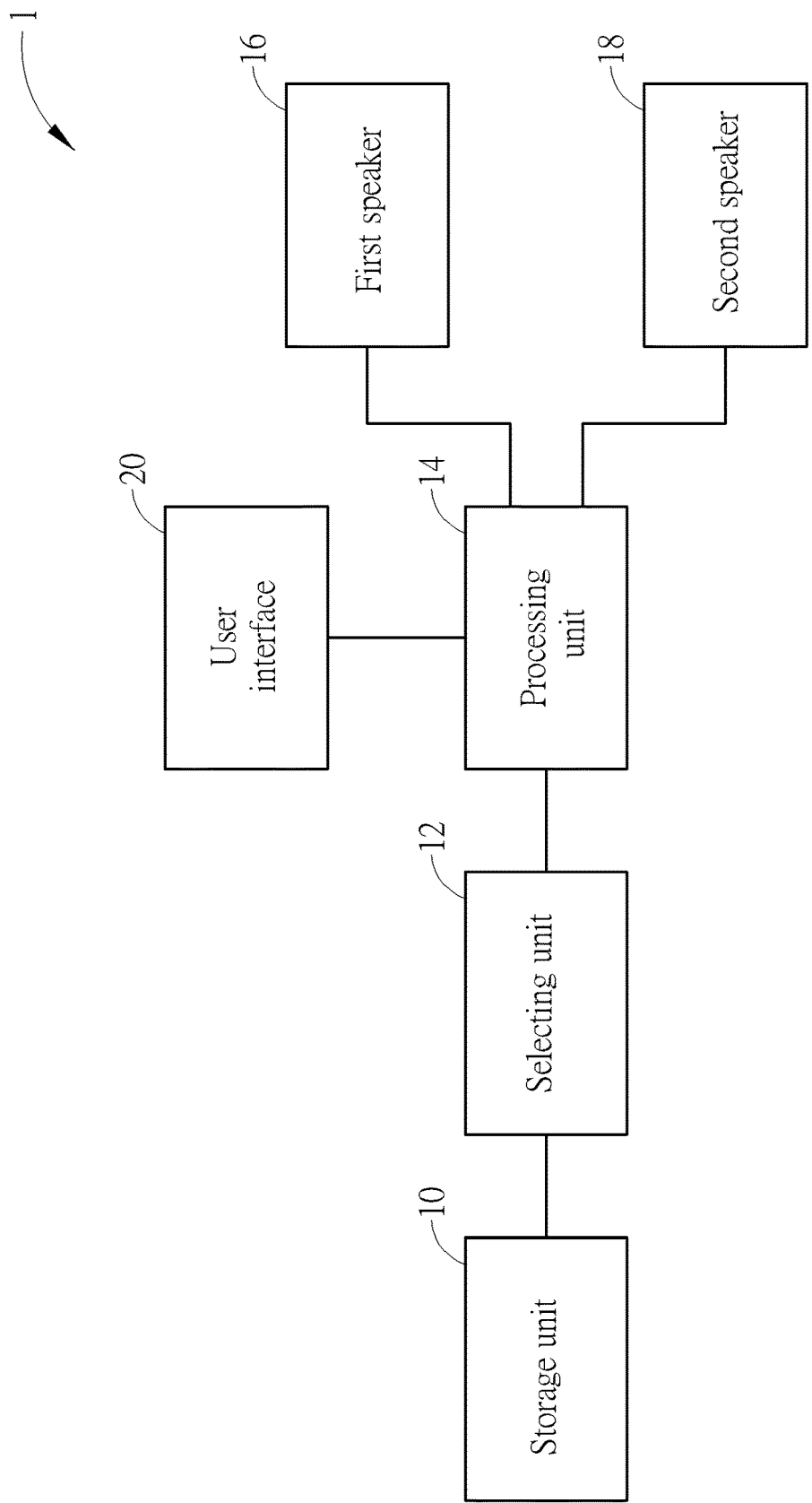
FIG. 1 is a functional block diagram illustrating an audio frequency generating device according to an embodiment of the invention.
Figure 2:
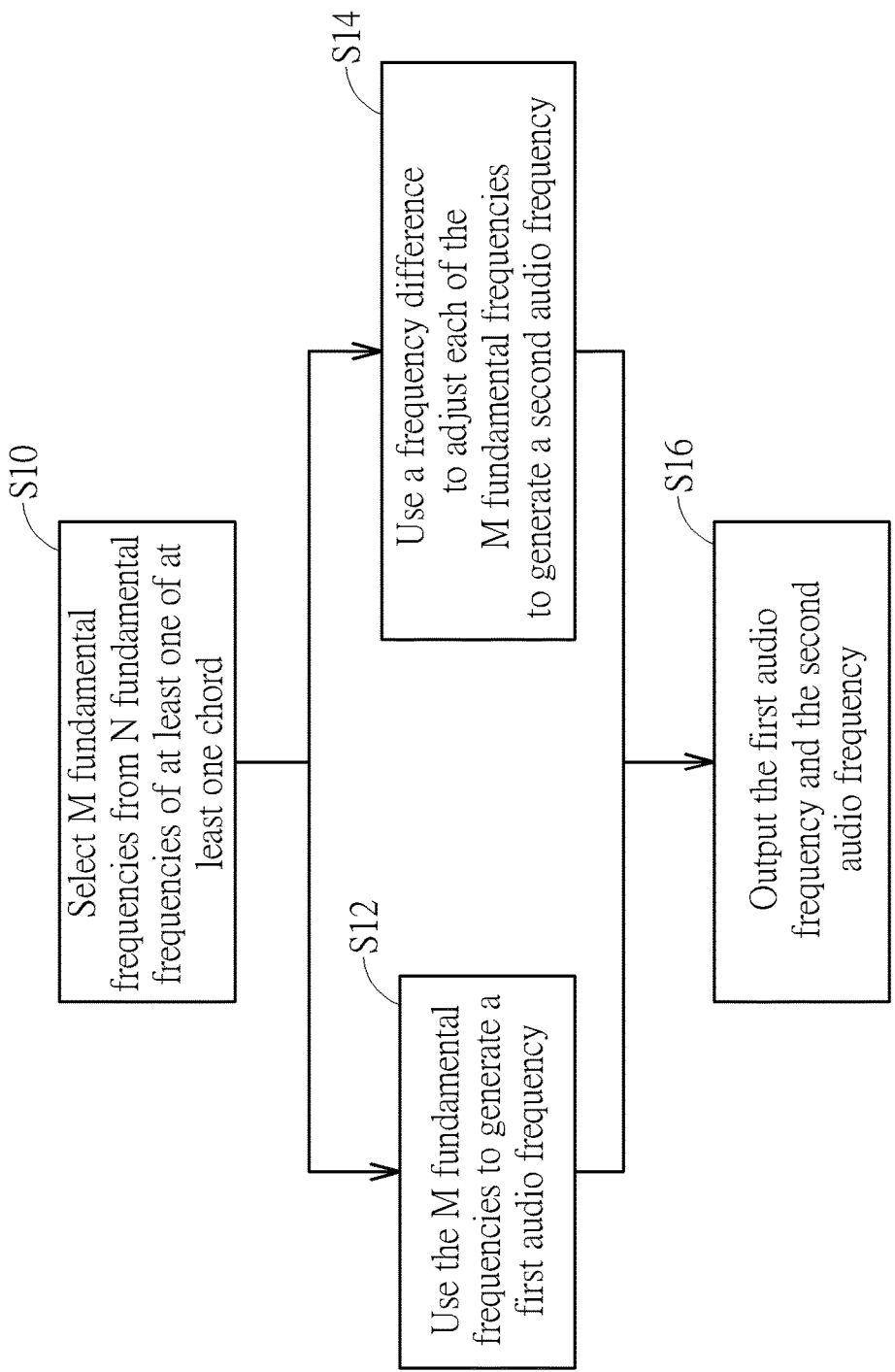
FIG. 2 is a flowchart illustrating an audio frequency generating method according to an embodiment of the invention.

Referring to FIGS. 1 and 2, FIG. 1 is a functional block diagram illustrating an audio frequency generating device 1 according to an embodiment of the invention and FIG. 2 is a flowchart illustrating an audio frequency generating method according to an embodiment of the invention. The audio frequency generating method shown in FIG. 2 can be implemented by the audio frequency generating device 1 shown in FIG. 1.

As shown in FIG. 1, the audio frequency generating device 1 comprises a storage unit 10, a selecting unit 12, a processing unit 14, a first speaker 16, a second speaker 18 and a user interface 20, wherein the selecting unit 12 is electrically connected to the storage unit 10 and the processing unit 14 is electrically connected to the selecting unit 12, the first speaker 16, the second speaker 18 and the user interface 20. In practical applications, the audio frequency generating device 1 may be an earphone, a headrest or other audio players; the storage unit 10 may be a memory, a hard disc or other data storage devices; the selecting unit 12 may be a signal selector; the processing unit 14 may be a processor or a controller with data processing function; the user interface 20 may be a touch display panel or other input devices. In general, the audio frequency generating device 1 may be further equipped with some necessary hardware or software components for specific purposes, such as an input/output port, applications, a circuit board, a power supply, etc., and it depends on practical applications.

The storage unit 10 stores at least one chord and each chord comprises N fundamental frequencies, wherein N is a positive integer larger than one. For example, the storage unit 10 may store C major chord and G major 7 chord, wherein the C major chord comprises three fundamental frequencies including 261.63 Hz, 329.63 Hz and 392.00 Hz, and the G major 7 chord comprises four fundamental frequencies including 196.00 Hz, 246.94 Hz, 293.66 Hz and 369.99 Hz. Accordingly, for the C major chord, N is equal to 3; and for the G major 7 chord, N is equal to 4. It should be noted that different chords may comprise identical or different number of fundamental frequencies and it depends on the type of the chord. Furthermore, the storage unit 10 may store one or more chords according to practical applications, so the invention is not limited to the aforesaid embodiment.

When the audio frequency generating device 1 is turned on to generate binaural beats, the selecting unit 12 selects M fundamental frequencies from the N fundamental frequencies of at least one of the at least one chord (step S10 in FIG. 2), wherein M is a positive integer larger than one and smaller than or equal to N. Then, the processing unit 14 uses the M fundamental frequencies to generate a first audio frequency (step S12 in FIG. 2). Furthermore, the processing unit 14 uses a frequency difference d to adjust each of the M fundamental frequencies to generate a second audio frequency (step S14 in FIG. 2). In this embodiment, the processing unit 14 may add the frequency difference d to each of the M fundamental frequencies to generate the second audio frequency. In another embodiment, the processing unit 14 may subtract the frequency difference d from each of the M fundamental frequencies to generate the second audio frequency.

As shown in Table 1 below, the processing unit 14 may generate the first audio frequency and the second audio frequency according to different selected chords and fundamental frequencies correspondingly. It should be noted that the chord and the fundamental frequency may be selected according to practical applications, so the invention is not limited to the embodiment shown in Table 1.

TABLE 1

| Selected chord and fundamental frequency | First audio frequency | Second audio frequency |
| --- | --- | --- |
| Three fundamental frequencies including 261.63 Hz, 329.63 Hz and 392.00 Hz of C major chord (i.e. M = 3) | 261.63 Hz, 329.63 Hz and 392.00 Hz | 261.63+d Hz, 329.63+d Hz and 392.00+d Hz |
| Three fundamental frequencies including 261.63 Hz, 329.63 Hz and 392.00 Hz of C major chord (i.e. M = 3) | 261.63 Hz, 329.63 Hz and 392.00 Hz | 261.63−d Hz, 329.63−d Hz and 392.00−d Hz |
| Two fundamental frequencies including 293.66 Hz and 369.99 Hz of G major 7 chord (i.e. M = 2) | 293.66 Hz and 369.99 Hz | 293.66+d Hz and 369.99+d Hz |
| Two fundamental frequencies including 261.63 Hz and 392.00 Hz of C major chord (i.e. M = 2) | 261.63 Hz, 392.00 Hz, 196.00 Hz, 246.94 Hz, 293.66 Hz and 369.99 Hz | 261.63−d Hz, 392.00−d Hz, 196.00−d Hz, 246.94−d Hz, 293.66−d Hz and 369.99−d Hz |
| Four fundamental frequencies including 196.00 Hz, 246.94 Hz, 293.66 Hz and 369.99 Hz of G major 7 chord (i.e. M = 4) | | |

In this embodiment, the frequency difference d may be selected from delta brainwave frequency band (0.5-3.5 Hz), theta brainwave frequency band (4-7 Hz), alpha brainwave frequency band (8-12 Hz), beta brainwave frequency band (13-28 Hz), or gamma brainwave frequency band (28+Hz). For example, if the audio frequency generating device 1 is used to generate binaural beats for enhancing attention, the frequency difference d may be selected from beta brainwave frequency band (e.g. 16 Hz); if the audio frequency generating device 1 is used to generate binaural beats for improving sleep, the frequency difference d may be selected from delta brainwave frequency band (e.g. 2 Hz); if the audio frequency generating device 1 is used to generate binaural beats for relaxation, the frequency difference d may be selected from alpha brainwave frequency band (e.g. 10 Hz); and so on.

Furthermore, the processing unit 14 may use different frequency differences d to adjust the M fundamental frequencies of an identical chord. For example, if three fundamental frequencies including 261.63 Hz, 329.63 Hz and 392.00 Hz of C major chord are selected to generate binaural beats for enhancing attention, the frequency differences d corresponding to the three fundamental frequencies including 261.63 Hz, 329.63 Hz and 392.00 Hz may be 14 Hz, 16 Hz and 18 Hz of beta brainwave frequency band. At this time, the processing unit 14 may generate the first audio frequency and the second audio frequency shown in Table 2 below.

TABLE 2

| First audio frequency | Second audio frequency |
| --- | --- |
| 261.63 Hz, 329.63 Hz and 392.00 Hz | 275.63 Hz, 345.63 Hz and 410.00 Hz |
| 261.63 Hz, 329.63 Hz and 392.00 Hz | 247.63 Hz, 313.63 Hz and 374.00 Hz |

Needless to say, the processing unit 14 may use an identical frequency difference d to adjust the M fundamental frequencies of an identical chord according to practical applications. Still further, the processing unit 14 may sharp or flat the selected fundamental frequencies of chord first and then use the frequency difference d to adjust the fundamental frequencies.

After generating the first audio frequency and the second audio frequency, the processing unit 14 controls the first speaker 16 to output the first audio frequency and controls the second speaker 18 to output the second audio frequency (step S16 in FIG. 2). In this embodiment, the first speaker 16 may output the first audio frequency for a left ear of a user and the second speaker 18 may output the second audio frequency for a right ear of the user. In another embodiment, the first speaker 16 may output the first audio frequency for a right ear of a user and the second speaker 18 may output the second audio frequency for a left ear of the user. It should be noted that the first audio frequency and the second audio frequency may be remixed with other music before being outputting, such that the binaural beats will not be too dissonant for hearing.

In this embodiment, the user interface 20 is configured to select at least one of the at least one chord and the frequency difference d by a user. For further description, the user may operate the user interface 20 to select the chord for generating binaural beats. Moreover, the user may also operate the user interface 20 to select the frequency difference d according to the required binaural beats correspondingly. Needless to say, the chord and the fundamental frequencies may be selected by system default according to practical applications.

As mentioned in the above, the invention uses at least two fundamental frequencies of at least one chord to generate binaural beats including the first audio frequency and the second audio frequency. Since the chord is more consonant for hearing, a user will not feel uncomfortable after listening to the binaural beats generated using the chord by the invention for a span of time.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An audio frequency generating device comprising:
a storage unit storing at least one chord, each of the at least one chord comprising N fundamental frequencies, N being a positive integer larger than one;
a selecting unit electrically connected to the storage unit, the selecting unit selecting M fundamental frequencies from the N fundamental frequencies of at least one of the at least one chord, M being a positive integer larger than one and smaller than or equal to N;
a processing unit electrically connected to the selecting unit, the processing unit using the M fundamental frequencies to generate a first audio frequency, the processing unit using a frequency difference to adjust each of the M fundamental frequencies to generate a second audio frequency;
a first speaker electrically connected to the processing unit, the first speaker outputting the first audio frequency; and
a second speaker electrically connected to the processing unit, the second speaker outputting the second audio frequency.

2. The audio frequency generating device of claim 1, wherein the frequency difference is selected from delta brainwave frequency band, theta brainwave frequency band, alpha brainwave frequency band, beta brainwave frequency band, or gamma brainwave frequency band.

3. The audio frequency generating device of claim 1, further comprising a user interface electrically connected to the processing unit, the user interface being configured to select at least one of the at least one chord and the frequency difference.

4. The audio frequency generating device of claim 1, wherein the processing unit adds the frequency difference to each of the M fundamental frequencies to generate the second audio frequency.

5. The audio frequency generating device of claim 1, wherein the processing unit subtracts the frequency difference from each of the M fundamental frequencies to generate the second audio frequency.

6. The audio frequency generating device of claim 1, wherein the processing unit uses different frequency differences to adjust the M fundamental frequencies of an identical chord.

7. An audio frequency generating method comprising steps of:
selecting M fundamental frequencies from N fundamental frequencies of at least one of at least one chord, wherein N is a positive integer larger than one and M is a positive integer larger than one and smaller than or equal to N;
using the M fundamental frequencies to generate a first audio frequency;
using a frequency difference to adjust each of the M fundamental frequencies to generate a second audio frequency; and
outputting the first audio frequency and the second audio frequency.

8. The audio frequency generating method of claim 7, wherein the frequency difference is selected from delta brainwave frequency band, theta brainwave frequency band, alpha brainwave frequency band, beta brainwave frequency band, or gamma brainwave frequency band.

9. The audio frequency generating method of claim 7, further comprising step of:
operating a user interface to select at least one of the at least one chord and the frequency difference.

10. The audio frequency generating method of claim 7, wherein the step of using a frequency difference to adjust each of the M fundamental frequencies comprises step of:
adding the frequency difference to each of the M fundamental frequencies.

11. The audio frequency generating method of claim 7, wherein the step of using a frequency difference to adjust each of the M fundamental frequencies comprises step of:
subtracting the frequency difference from each of the M fundamental frequencies.

12. The audio frequency generating method of claim 7, wherein the step of using a frequency difference to adjust each of the M fundamental frequencies comprises step of:
using different frequency differences to adjust the M fundamental frequencies of an identical chord.

* * * * *